United States Patent
Mashburn (10) Patent No.: US 7,022,138 B2
(45) Date of Patent: Apr. 4, 2006

(54) SPINAL INTERBODY FUSION DEVICE AND METHOD

(76) Inventor: M. Laine Mashburn, 248 Bird Haven La., Ether, NC (US) 27247

( * ) Notice: Subject to any disclaimer, the term of this patent is extended or adjusted under 35 U.S.C. 154(b) by 129 days.

(21) Appl. No.: 10/631,621

(22) Filed: Jul. 31, 2003

(65) Prior Publication Data

US 2005/0027359 A1 Feb. 3, 2005

(51) Int. Cl.
*A61F 2/44* (2006.01)
(52) U.S. Cl. .................. 623/17.13; 623/17.11; 623/17.15; 623/17.16; 606/61
(58) Field of Classification Search .......... 606/61, 606/63, 76, 78; 623/17.11, 17.12, 17.13, 623/17.15, 17.16, 23.47, 23.5
See application file for complete search history.

(56) References Cited

U.S. PATENT DOCUMENTS

| | | | | |
|---|---|---|---|---|
| 4,289,123 A | | 9/1981 | Dunn | 128/84 |
| 4,401,112 A | * | 8/1983 | Rezaian | 606/61 |
| 4,553,273 A | * | 11/1985 | Wu | 623/23.45 |
| 4,657,550 A | * | 4/1987 | Daher | 623/17.11 |
| 4,938,768 A | * | 7/1990 | Wu | 623/23.47 |
| 5,154,718 A | * | 10/1992 | Cozad et al. | 606/61 |
| 5,246,458 A | * | 9/1993 | Graham | 623/17.14 |
| 5,336,223 A | * | 8/1994 | Rogers | 606/61 |
| 5,413,602 A | * | 5/1995 | Metz-Stavenhagen | 623/17.15 |
| 5,458,641 A | * | 10/1995 | Ramirez Jimenez | 623/17.11 |
| 5,480,442 A | | 1/1996 | Bertagnoli | 623/17 |
| 5,607,424 A | * | 3/1997 | Tropiano | 606/61 |
| 5,676,702 A | * | 10/1997 | Ratron | 623/17.16 |
| 5,683,464 A | | 11/1997 | Wagner et al. | 623/17 |
| 5,702,453 A | | 12/1997 | Rabbe et al. | 623/17 |
| 5,702,455 A | * | 12/1997 | Saggar | 623/17.15 |
| 5,766,252 A | * | 6/1998 | Henry et al. | 623/17.16 |
| 5,776,197 A | | 7/1998 | Rabbe et al. | 623/17 |
| 5,776,198 A | * | 7/1998 | Rabbe et al. | 623/17.15 |
| 5,888,224 A | * | 3/1999 | Beckers et al. | 623/17.16 |
| 6,015,436 A | | 1/2000 | Schönhöffer | 623/17 |
| 6,176,881 B1 | | 1/2001 | Schär et al. | 623/17.11 |
| 6,193,755 B1 | * | 2/2001 | Metz-Stavenhagen et al. | 623/17.11 |
| 6,245,108 B1 | * | 6/2001 | Biscup | 623/17.11 |
| 6,379,355 B1 | * | 4/2002 | Zucherman et al. | 606/61 |
| 6,454,806 B1 | * | 9/2002 | Cohen et al. | 623/17.15 |
| 6,468,311 B1 | * | 10/2002 | Boyd et al. | 623/17.16 |

(Continued)

FOREIGN PATENT DOCUMENTS

EP 1 080 703 A2 8/2000
WO WO 03/096937 A1 11/2003

OTHER PUBLICATIONS

Book entitled "Biomechanics of Spine Stabilization Principles and Clinical Procedures" by Edward C. Benzel; 278 pages; Copyright 1995.

*Primary Examiner*—Eduardo C. Robert
*Assistant Examiner*—David Comstock (57) ABSTRACT

A disc replacement spinal interbody fusion device is provided having a central sleeve with oppositely left and right-hand threaded axial bores with different diameters. Circumferential threaded apertures are located on the sleeve and open into the sleeve bores. The device has two opposing plates which are oval-shaped and centrally, axially bored. Each plate has a perpendicular shaft with an axial bore which communicates with the plate bore. In situ, axial loading of the spinal column upon the fusion device creates a bending moment manifested by a flexing action of the plates to generate opposing axial directional forces which replicate the physiological function of shock absorption, load bearing and load transmission.

21 Claims, 5 Drawing Sheets

U.S. PATENT DOCUMENTS

| | | | |
|---|---|---|---|
| 6,524,341 B1 | 2/2003 | Läng et al. | 623/17.15 |
| 6,660,038 B1 * | 12/2003 | Boyer et al. | 623/17.15 |
| 6,695,842 B1 * | 2/2004 | Zucherman et al. | 606/61 |
| 6,866,682 B1 * | 3/2005 | An et al. | 623/17.15 |
| 2002/0161441 A1 * | 10/2002 | Lang et al. | 623/17.11 |
| 2002/0161443 A1 * | 10/2002 | Michelson | 623/17.11 |
| 2004/0167626 A1 * | 8/2004 | Geremakis et al. | 623/17.15 |

* cited by examiner

SPINAL INTERBODY FUSION DEVICE AND METHOD

FIELD OF THE INVENTION

The present invention relates to a device and method designed to anatomically and physiologically replace a damaged spinal disc and to assist in fusing adjacent vertebra to stabilize the spine.

DESCRIPTION OF THE PRIOR ART AND OBJECTIVES OF THE INVENTION

The most appropriate technique currently used by spinal surgeons in the treatment of disc disorders is removal and replacement of an affected disc utilizing an anterior or anterolateral approach to the disc site. Removal of the disc causes an instability which must be corrected by disc replacement and bone grafting to restore the anatomical height and physiological function of shock absorption, load support and load transmission.

Replacement materials currently favored are bone graft blocks or titanium mesh cages filled with disintegrated bone graft, both of which are held in place by anteriolateral or posterior fixation. In lumbar disc replacement, static mesh cages fill and fuse the disc space but do not effectively absorb shock or support and transmit spinal loads. Bone graft blocks have the additional disadvantage of time-consuming intraoperative preparation. It is therefore an objective of the present invention to provide a manually expandable spinal interbody fusion device and method for replacement of a removed spinal disc for different disc spaces which vary in height.

It is another objective of the present invention to provide a durable spinal interbody fusion device which is formed from a titanium alloy configured for shock absorption.

It is also an objective of the present invention to provide a spinal interbody fusion device which can be contracted so as to be easily inserted, expanded and locked in its vertically expanded posture between spinal vertebrae.

It is still another objective of the present invention to provide a spinal interbody fusion device which allows vertebrae fusion through its central channel.

It is a further objective of the present invention to provide a spinal interbody fusion device which includes a first plate and a second plate, each of which have a gradual posterior bias to conform to the anatomy of the lumbar spine vertebrae.

Finally, it is an objective to provide a spinal interbody fusion device which restores the physiological function of shock absorption, load support and load transmission.

The aforesaid and other objectives and advantages will become apparent to those skilled in the art as a more detailed description is set forth below.

SUMMARY OF THE INVENTION

The aforesaid and other objectives are realized by providing a vertically expandable spinal interbody fusion device of titanium alloy for surgically replacing a spinal disc. The device is designed for spinal disc space fusion and shock absorption as well as support and transmission of spinal loads while enhancing the replication of the physiological function of the spinal column.

The spinal interbody fusion device is intraoperatively assembled by left and right-hand threading of opposing perpendicular shafts of two (2) plates into ends of a central sleeve to create a turnbuckle-like effect. To accommodate bone fusion through the core or channel of the fusion device, each plate and shaft is centrally bored while surrounding apertures in each plate provide for peripheral fusion. Additionally, to fill bone graft voids created by expansion, each shaft has threadless circumferential access apertures at the plate shaft junctures. The upper or first plate has a gradual posterior decline and the lower or second plate has a gradual posterior incline to conform to the configuration of the space between lumbar spine vertebrae.

The first shaft has external left-hand threads and the second shaft has external right-hand threads, each to mate with different bores of the sleeve. The outside diameter of the first shaft is smaller than the inside diameter of the second shaft, allowing the two shafts to axially engage. The spinal interbody fusion device operates like a turnbuckle, vertically expanding when the sleeve is rotated in one direction and retracting when the sleeve is rotated in the opposite direction. The assembled device defines an open channel axially. Once the fusion device is set at its proper height, set screws are threaded into circumferential apertures of the sleeve to compress against the shaft threads of each plate to maintain a fixed height.

The method includes assembly of the fusion device during which the plate shafts are opposingly threaded into the central sleeve. The first shaft selectively descends inside the large bore of the second shaft, which is sized for accommodation thereof, until the fusion device is fully contracted. The channel of the fusion device is filled with bone graft through the connecting bores of the plates and shafts. The fusion device is then inserted into the surgically prepared disc space of the patient's spine at the minimal height of the fusion device and, by rotating the sleeve in one direction, the fusion device is vertically expanded until the surfaces of the plates compress against the exposed horizontal surfaces of the adjacent vertebrae at the correct anatomical angle. The fusion device is then locked together with set screws inserted through apertures in the side of the sleeve and against the plate shafts. The heads of the set screws can be broken away and after bone graft voids within the channel are filled via the circumferential access apertures, the device is then surrounded with additional bone graft so that fusion will occur both through and around the device. Finally, the correct position of the device is secured with conventional anteriolateral or posterior instruments.

The method as described results in a stable disc replacement with a secure interface between the plates of the spinal interbody fusion device and the horizontal surfaces of the adjacent vertebrae. Additionally, each plate has a roughened outer surface to create a high frictional coefficient with the vertebra in order to resist translational and rotational movement. Each plate moreover has an oval shape to conform to the horizontal configuration of an adjacent vertebra in order to avoid injury to surrounding blood vessels. Each plate diameter is significantly greater in area than the diameter of its corresponding shaft, defining a lever arm to produce a bending moment under spinal loads manifested by action of each plate. This flexing action generates opposing axial forces to replicate the normal physiological function of shock absorption, load bearing and load transmission.

DETAILED DESCRIPTION OF THE PREFERRED EMBODIMENTS AND OPERATION OF THE INVENTION

Figure 1:
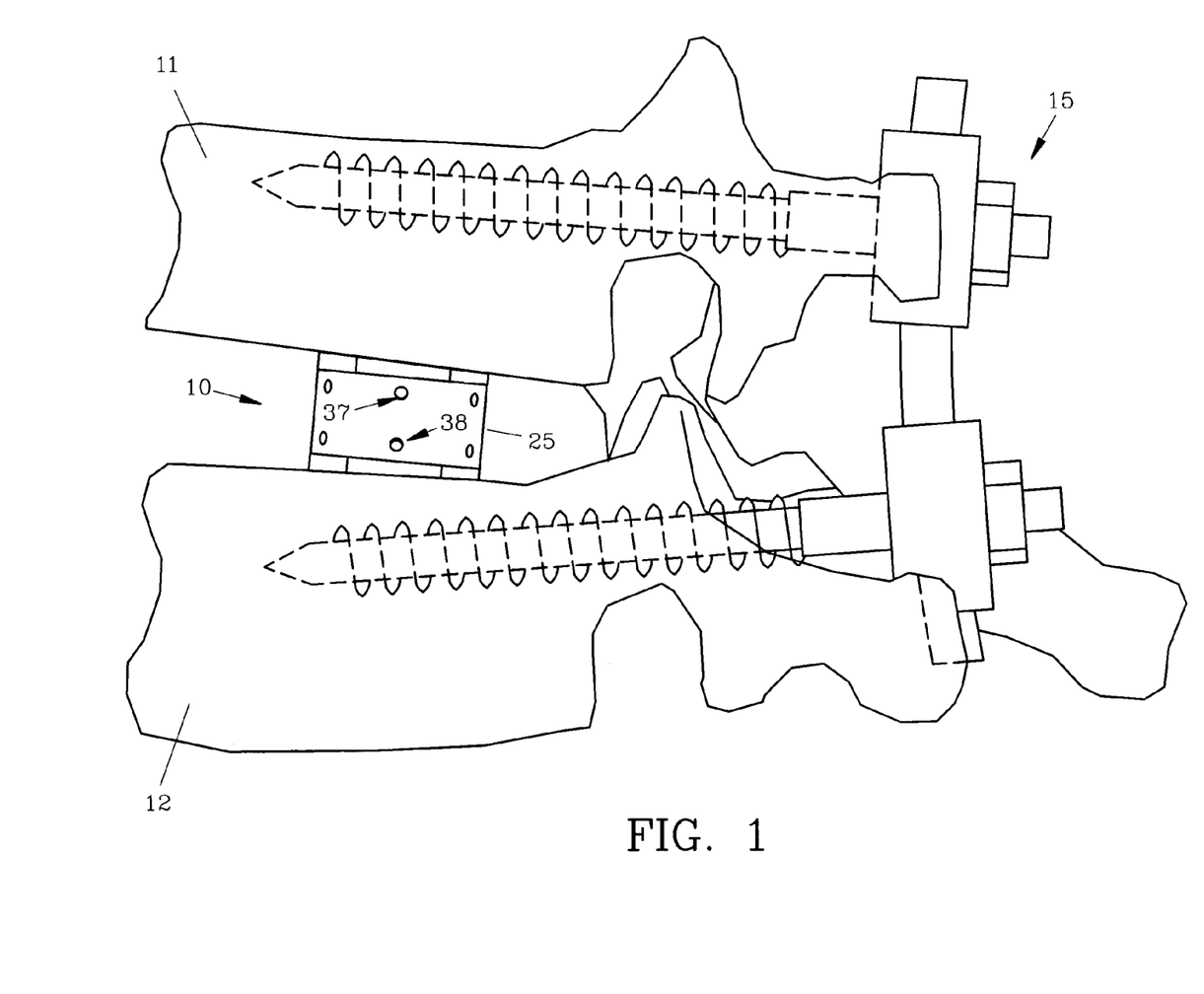
FIG. 1 demonstrates a schematic side view of the spinal interbody fusion device in a contracted posture of a typical implantation between contiguous vertebrae.

For a better understanding of the invention and its operation, turning now to the drawings, FIG. 1 illustrates preferred spinal interbody fusion device 10 in its fully contracted posture positioned between adjacent vertebra 11, 12. Conventional spinal fixation instrumentation 15 is also shown to contain the spine in a suitable posture after positioning and adjusting of fusion device 10.

Figure 2:
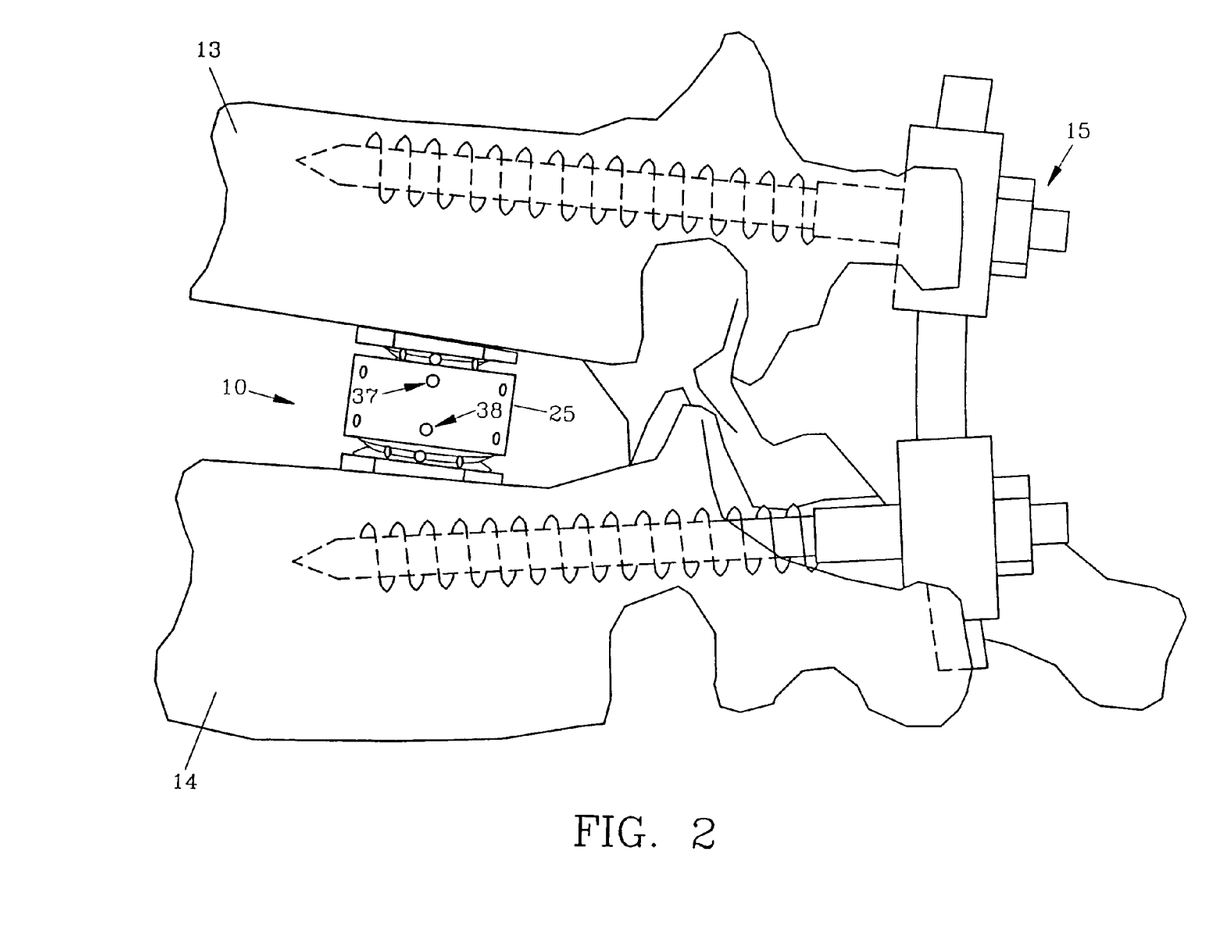
FIG. 2 shows a schematic side view of another typical implantation but with the spinal interbody fusion device somewhat expanded to accommodate a greater distance between adjacent vertebrae.

In FIG. 2, spinal interbody fusion device 10 is seen placed between another pair of vertebra 13, 14 which are spaced somewhat farther apart than those shown in FIG. 1, requiring fusion device 10 to be slightly expanded as will hereinafter be more fully described.

Figure 3:
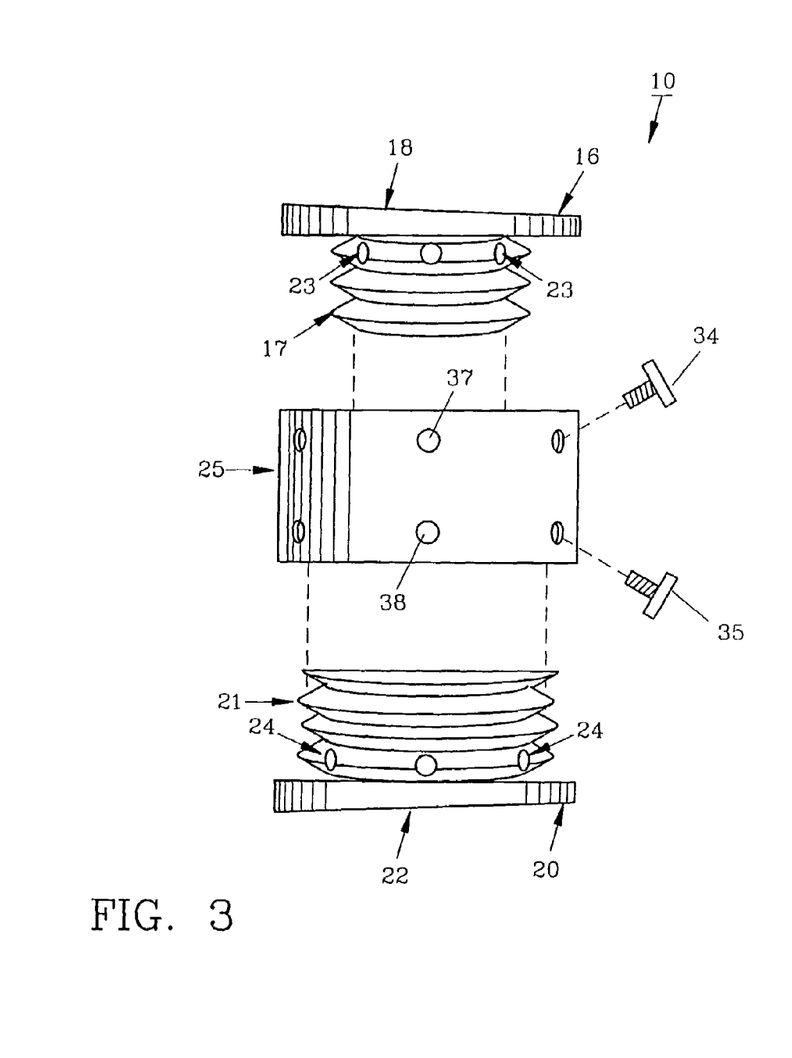
FIG. 3 features an exploded enlarged side view of the spinal interbody fusion device of the invention.
Figure 4:
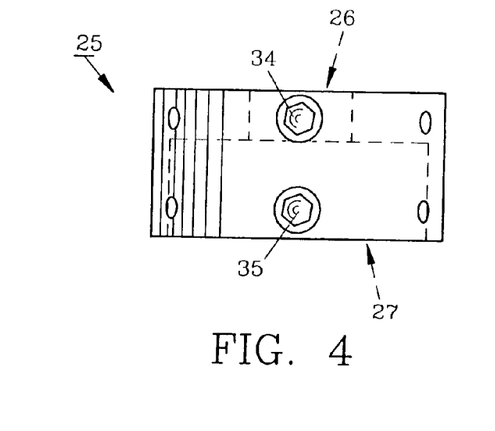
FIG. 4 pictures an enlarged side view of the spinal interbody fusion device sleeve.
Figure 5:
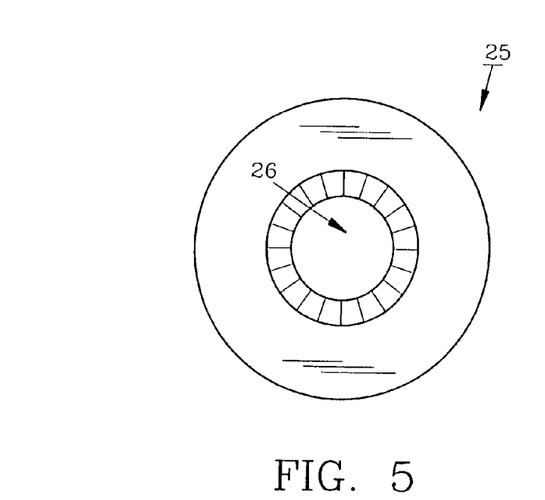
FIG. 5 illustrates a top view of the spinal interbody fusion device sleeve as seen in FIG. 4.
Figure 6:
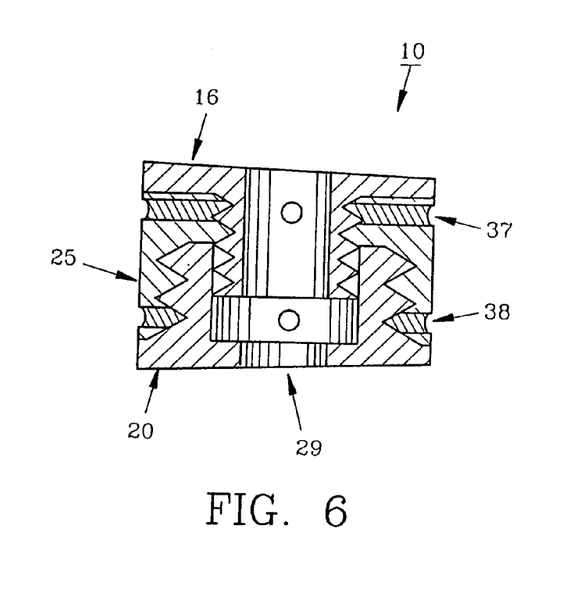
FIG. 6 depicts a cross-sectional side view of the spinal interbody fusion device as assembled.

In FIG. 3, an enlarged view of fusion device 10 is shown in exploded fashion with upper or first plate 16 rigidly affixed to first threaded shaft 17, preferably having an outside diameter in the range of eleven (11) millimeters with an inside diameter of approximately seven (7) millimeters. Similarly, lower or second plate 20 is rigidly attached to second threaded shaft 21 which preferably has an outside diameter of approximately sixteen (16) millimeters with an inside diameter in the range of twelve (12) millimeters until it reaches plate 20 where the inside diameter is reduced to approximately seven (7) millimeters. First shaft 17 and second shaft 21 have circumferential threadless apertures 23, 24 at each plate/shaft juncture. Plates 16, 20 are horizontally and opposingly biased and can vary in size with the median size preferably being approximately thirty (30) millimeters in the medial/lateral dimension and approximately twenty (20) millimeters in the anterior/posterior dimension. Plate 16 has a gradual posterior decline, whereas plate 20 has a gradual posterior incline. The decline and incline of plates 16, 20 are between 0.5 and 5.0 degrees from the horizontal and preferably being approximately 3.0 degrees from the horizontal. Shafts 17 and 21 threadably connect within central sleeve 25 which preferably is cylindrical in shape and has a height of approximately seven (7) millimeters with an outside diameter in the range of twenty (20) millimeters and includes a first threaded channel 26 having an inside diameter in the range of eleven (11) millimeters and a second, larger diameter threaded channel 27 having an inside diameter in the range of sixteen (16) millimeters as shown in FIGS. 4, 5 and 6. As also seen in FIG. 6, spinal interbody fusion device 10 when assembled provides a continuous bore or channel 29, extending from first plate 16 through second plate 20, to accept bone graft for bone growth and fusion completely therethrough. As seen in FIG. 3, first and second shafts 17, 21 have equally-spaced circumferential threadless apertures 23, 24 at each plate/shaft juncture so that additional bone graft can be inserted into channel 29 after in-situ placement of spinal interbody fusion device 10 to fill voids created by vertical expansion (as seen in FIG. 2). Shaft 17 is sized to retract into shaft 21 so that spinal interbody fusion device 10 can be contracted to facilitate insertion between either vertebrae 11, 12 or 13, 14 and to provide a variety of height options as well as to provide unobstructed continuous channel 29. Shaft 17 has left-handed threads whereby shaft 21 has right-handed threads to allow sleeve 25 to rotate in one direction to simultaneously extend shafts 17, 21 and to rotate in the opposite direction to retract both shafts 17, 21 simultaneously as required during implantation.

Figure 7:
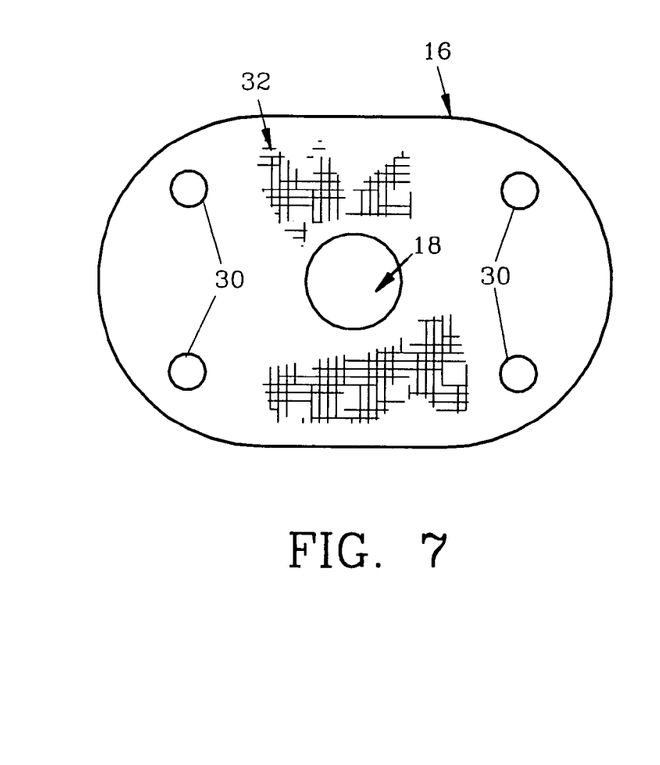
FIG. 7 illustrates a top plan view of the assembled spinal interbody fusion device.
Figure 8:
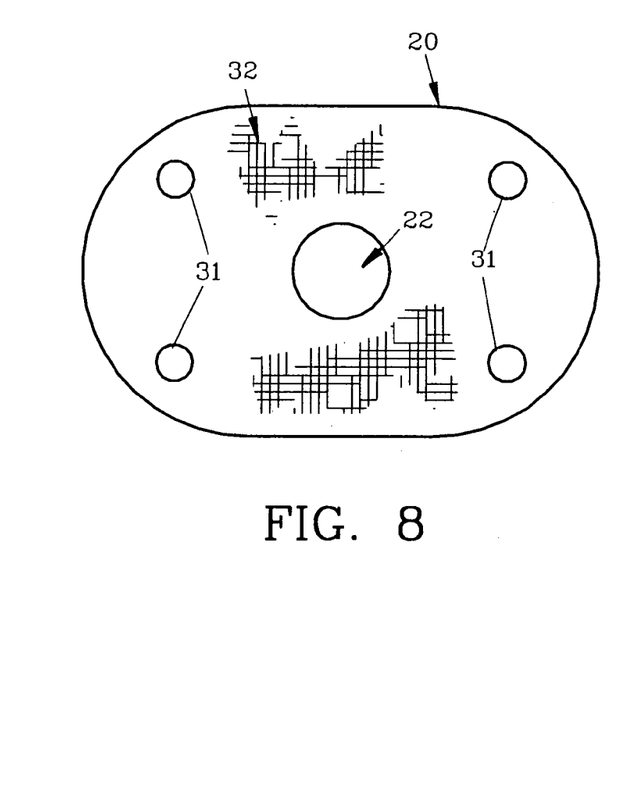
FIG. 8 pictures a bottom plan view of the assembled spinal interbody fusion device.

As shown in FIGS. 7 and 8, plate 16 includes threadless top bore 18 having preferably an inside diameter of approximately seven (7) millimeters. Likewise, second plate 20 includes threadless bottom bore 22 also preferably having an inside diameter in the range of seven (7) millimeters, being reduced at the plate surface from the larger inside diameter of second shaft 21, as shown in FIGS. 3 and 6. Threadless top and bottom bores 18, 22 (FIG. 3) have the same diameter to assure a match in core fusion diameter. Further, first and second plates 16, 20 both include a plurality of apertures 30, 31 therein to assist in adhesion of fusion device 10 to the adjacent vertebra during spinal bone growth. Plates 16, 20 have diameters which are significantly larger than respective diameters of shafts 17, 21, defining a lever arm to produce a bending moment under spinal loads manifested by action of each plate. This flexing action generates opposing axial forces to replicate the physiological function of shock absorption, load bearing and load transmission.

To improve the coefficient of friction and to prevent unwanted rotational movement, first plate 16 and second plate 20, which are oval in shape are flame-sprayed with a conventional titanium based coating 32 during manufacturing. This coating provides a roughened surface and a high coefficient of friction to assist in preventing rotational movement upon implantation.

Figure 9:
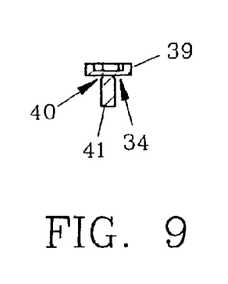
FIG. 9 shows a cross-sectional side view of a set screw as used with the spinal interbody fusion device.
Figure 10:
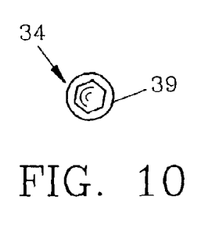
FIG. 10 features a top view of the set screw as seen in FIG. 9.

Sleeve 25 comprises a plurality of circumferential threaded apertures 37, 38 (preferably six (6) of each) to accept set screws 34, 35 shown in FIGS. 3, 9 and 10. Once spinal interbody fusion device 10 is in position and plates 16 and 20 are properly expanded and positioned against adjacent vertebra, set screws 34, 35 are threaded through the most accessible of apertures 37, 38 as shown in FIGS. 1 and 2 and by tightening contact respectively, threaded shafts 17, 21 to lock plates 16, 20 in place relative to sleeve 25. As shown in FIGS. 9 and 10, set screw 34 is designed to receive a screw driver with an allen-type wrench tip and includes a weakened neck area 40 shown in FIG. 9 whereby head 39 can be twisted and broken from screw shaft 41 shown in FIG. 11 to facilitate bone growth therearound. As would be understood set screw 34 is identical to set screw 35.

The preferred method of the invention includes the steps of assembling preferred spinal interbody fusion device 10 by threading first and second shafts 17, 21 into central sleeve 25 to approximate the disc space which spinal interbody fusion device 10 is to occupy. Next, continuous channel 29 of spinal interbody fusion device 10 is filled with bone graft.

Figure 11:
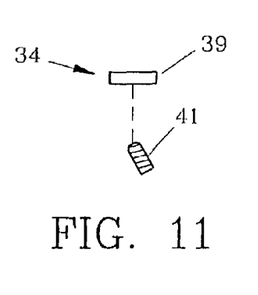
FIG. 11 demonstrates the set screw of FIG. 7 with the head broken therefrom.

Filled spinal interbody fusion device 10 is then inserted into the surgically prepared disc space between adjacent vertebra, such as between vertebra 11, 12 as shown in FIG. 1. By carefully rotating sleeve 25 in a clockwise or counter clockwise direction as required, plates 16, 20 can be suitably adjusted to contact the adjacent vertebra at the correct anatomical angle. Once properly positioned, spinal interbody fusion device 10 is then locked with set screws 34, 35 by tightening them through apertures 37, 38 seen in FIG. 1. By exerting additional pressure to set screw 34, 35 with a screwdriver having an allen or similar type wrench tip, head 39 of set screws 34, 35 can be broken away (FIG. 11). After filling any expansion-related bone graft voids in continuous channel 29, spinal interbody fusion device 10 can then be surrounded with additional bone graft for improved strength and permanency. The position of spinal interbody fusion device 10 can be further secured with conventional anteriolateral or posterior instruments such as fixation instrumentation 15 seen in FIGS. 1 and 2.

The illustrations and examples provided herein are for explanatory purposes and are not intended to limit the scope of the appended claims.

I claim:

1. A spinal interbody fusion device comprising: a sleeve, said sleeve defining a first and a second threaded channel, said first and said second sleeve channels in communication with each other, a first plate, said first plate defining a declining surface and a central bore through said first plate, a first threaded shaft, said first shaft attached to said first plate, said first shaft defining an axial bore therethrough, said first shaft bore in communication with said first plate bore, said first shaft threadably received in said first sleeve channel, a second plate, said second plate defining an inclining surface and a central bore through said second plate, a second threaded shaft, said second shaft affixed to said second plate and extending towards said first plate, said second shaft defining an axial bore therethrough, said second shaft bore in communication with said second plate bore, said second shaft threadably received in said sleeve second channel, said first shaft receivable in said second shaft bore, said first plate bore in communication with said second plate bore through said shafts and said sleeve, whereby a continuous bore through said spinal interbody fusion device is provided.

2. The spinal interbody fusion device of claim 1 wherein said first shaft is centered on said first plate, said first shaft extending perpendicularly from said first plate, said first plate extending radially beyond the outer diameter of said first shaft whereby loading said spinal interbody fusion device allows said first plate to operate as a lever arm creating a bending moment about said first shaft when the load is directed through said first plate.

3. The spinal interbody fusion device of claim 1 wherein said sleeve is cylindrically shaped, said first sleeve channel has a diameter smaller than said second sleeve channel, the outer diameter of said sleeve being substantially uniform, said first and said second plates each having a diameter at least equal to the outer diameter of said sleeve, the outer diameter of said sleeve being greater than an outer diameter of said first and said second shafts.

4. The spinal interbody fusion device of claim 1 wherein said first plate is oval-shaped, the lateral width of said first plate is greater than the depth of said first plate from the anterior to the posterior thereof, said first plate surface declining from the anterior to the posterior of said spinal interbody fusion device, whereby the thickness of said first plate diminishes posteriorly.

5. The spinal interbody fusion device of claim 4 wherein said first and said second plates have opposing horizontal biases whereby said spinal interbody fusion device is wedge-shaped.

6. The spinal interbody fusion device of claim 1 wherein said first and said second plate shafts each define an aperture, said first shaft aperture being contiguous said first plate while said second shaft aperture is contiguous said second plate, each of said first and said second shaft apertures in communication with said continuous central channel.

7. The spinal interbody fusion device of claim 1 wherein said sleeve defines a pair of threaded circumferential apertures, each of said sleeve apertures extending from the outer diameter of said sleeve to a different one of said sleeve channels.

8. The spinal interbody fusion device of claim 1 further comprises a friction coating, said friction coating contained on said first and said second plates.

9. The spinal interbody fusion device of claim 1 formed from metal.

10. The spinal interbody fusion device of claim 9 wherein said metal comprises a titanium alloy.

11. The spinal interbody fusion device of claim 1 wherein an outer diameter of said first shaft is less than an inner diameter of said second shaft to allow said first shaft to retract into said second shaft, said sleeve surrounding both said first and said second shafts.

12. A spinal interbody fusion device comprising: a sleeve, said sleeve being cylindrically-shaped and having a substantially uniform outer diameter, said sleeve defining a small first threaded axial channel and a large second threaded axial channel, said first sleeve channel in communication with said second sleeve channel, a first plate, said first plate defining a central bore therethrough and a substantially planar declining surface, a first threaded shaft, said first shaft affixed to said first plate, said first shaft extending from said first plate, said first shaft being externally threaded and defining an axial bore therethrough, said first shaft bore in communication with said first plate bore, said first shaft threadably received within said first sleeve channel, a second plate, said second plate defining a central bore therethrough and a substantially planar inclining surface, a second threaded shaft, said second shaft affixed to said second plate, said second shaft extending from said second plate towards said first plate, said second shaft being externally threaded and defining an axial bore, said second shaft bore being in communication with said second plate bore, said second shaft threadably secured within said second sleeve channel, each one of said first and said second plates is wider and deeper than each is thick, said first plate bore being in communication with said second plate bore through said first and said second shafts and said sleeve to provide a continuous bore completely through said spinal interbody fusion device whereby rotating said sleeve will extend said first and second plates from said sleeve.

13. The spinal interbody fusion device of claim 12 wherein said first and said second plates are oval-shaped and horizontally and opposingly inclined, the thickness of each of said plates diminishing towards the other whereby said spinal interbody fusion device is wedge-shaped from the anterior to the posterior thereof.

14. The spinal interbody fusion device of claim 12 wherein said first threaded shaft defines left-handed threads and said second threaded shaft defines right-handed threads, the outer diameter of said first shaft being less than the inner diameter of said second shaft, said first shaft being receivable in said second shaft.

15. The spinal interbody fusion device of claim 12 wherein said sleeve defines a pair of set screw apertures, each of said set screw apertures extending from the outer diameter of said sleeve to a different one of said sleeve channels therein.

16. The spinal interbody fusion device of claim 12 wherein each of said first and said second plates provide a friction producing oval-shaped surface.

17. The spinal interbody fusion device of claim 12 wherein each of said first and said second plates define a lever arm, each of said lever arms generating an axial force opposing the other when said spinal interbody fusion device is flexed.

18. A spinal fusion method utilizing a generally wedge-shaped spinal interbody fusion device having a pair of adjustable oval-shaped plates with opposing horizontal biases that diminish posteriorly, the first and second plates each having a central bore, a pair of externally threaded shafts, the first shaft extending from the first plate, the second shaft extending from the second plate towards the first shaft in axial alignment with the first shaft, the first and second shafts each defining an axial bore therethrough, the diameter of the second shaft bore being greater than the diameter of the first shaft and a sleeve having a first and a second channel with each channel threaded oppositely from and in communication with the other channel, the first and second sleeve channels threadably connected to the first and second shafts respectively, the sleeve being between the plates with a continuous central bore extending from the bore in the first plate to the bore in the second plate and through the shafts and the sleeve for accepting a bone graft therein for bone growth and fusion completely through the device while the plates overhang the shafts to allow opposing bending moments thereabout for shock absorption and the first shaft is retractable into the second shaft bore for sizing the device, the method comprising the steps of:

a) rotating the sleeve to cause the first shaft to be received in the second shaft bore;

b) removing the damaged disc between adjacent spinal vertebrae to form a space between the remaining adjacent spinal vertebrae ;

c) threadably adjusting the height of the fusion device to approximate the height of the space by rotating the sleeve whereby rotating the sleeve in a first direction retracts the first shaft into the second shaft;

d) filling the central bore of the device with a bone graft;

e) inserting the fusion device containing the bone graft within the space with each plate contiguous a different one of the adjacent spinal vertebrae while the opposing biases of the plates diminish posteriorly;

f) threadably adjusting the inserted fusion device to tightly accommodate the space between the adjacent vertebrae;

g) allowing the vertebrae to grow to the spinal interbody fusion device and bone graft; and h) generating opposing axial forces by flexing the interbody fusion device.

19. The method of claim 18 wherein adjusting the device to tightly accommodate the space comprises the step of increasing the height of the device by rotating the sleeve in an opposite direction to extend the shafts from the sleeve for engaging the adjacent spinal vertebrae with the plates.

20. The method of claim 19 wherein the step of adjusting the fusion device comprises the step of rotating the sleeve.

21. The method of claim 20 further comprising the step of locking the fusion device to its adjusted position by tightening a set screw into the sleeve and engaging one of said shafts.

* * * * *